United States Patent
Chan et al.

(10) Patent No.: US 10,194,831 B2
(45) Date of Patent: Feb. 5, 2019

(54) APPARATUS, SYSTEM AND METHOD FOR IMAGING AND TREATMENT USING OPTICAL POSITION SENSING

(75) Inventors: Raymond Chan, San Diego, CA (US); Guy Shechter, Briarcliff Manor, NY (US); Adrien Emmanuel Desjardins, Waterloo (CA); Gert 'T Hooft, Eindhoven (NL); Christopher Stephen Hall, Hopewell Junction, NY (US)

(73) Assignee: Koninklijke Philips N.V., Eindhoven (NL)

( * ) Notice: Subject to any disclaimer, the term of this patent is extended or adjusted under 35 U.S.C. 154(b) by 1242 days.

(21) Appl. No.: 13/577,268

(22) PCT Filed: Jan. 14, 2011

(86) PCT No.: PCT/IB2011/050169
§ 371 (c)(1),
(2), (4) Date: Dec. 7, 2012

(87) PCT Pub. No.: WO2011/098926
PCT Pub. Date: Aug. 18, 2011

(65) Prior Publication Data
US 2013/0131499 A1 May 23, 2013

Related U.S. Application Data

(60) Provisional application No. 61/302,571, filed on Feb. 9, 2010.

(51) Int. Cl.
*A61B 5/06* (2006.01)
*A61B 8/12* (2006.01)
(Continued)

(52) U.S. Cl.
CPC ............ *A61B 5/065* (2013.01); *A61B 8/0841* (2013.01); *A61B 8/12* (2013.01); *A61B 8/4245* (2013.01);
(Continued)

(58) Field of Classification Search
CPC ........ A61B 19/5244; A61B 1/07; A61B 5/065
See application file for complete search history.

(56) References Cited

U.S. PATENT DOCUMENTS 6,287,260 B1 * 9/2001 Hascoet ................... A61B 8/06
600/454
6,612,992 B1 9/2003 Hossack et al.
(Continued)

FOREIGN PATENT DOCUMENTS

JP 1997154843 A 6/1997
JP 2001046387 A 2/2001
(Continued)

*Primary Examiner* — Rochelle Turchen (57) ABSTRACT

An apparatus, system and method for determining a position includes a transducer device (102) configured to receive signals from a console (104) and generate images based upon reflected waves. A flexible cable (108) is coupled to the transducer device to provide excitation energy to the transducer device from the console. An optical fiber (110) has a shape and position corresponding to a shape and position of the cable during operation. A plurality of sensors (122) is in optical communication with the optical fiber. The sensors are configured to measure deflections and bending in the optical fiber such that the deflections and bending in the optical fiber are employed to determine positional information about the transducer device.

4 Claims, 6 Drawing Sheets

(51) Int. Cl.
*A61B 8/00* (2006.01)
*A61B 8/08* (2006.01)
*A61N 7/02* (2006.01)
*A61B 34/20* (2016.01)

(52) U.S. Cl.
CPC .......... *A61B 8/4254* (2013.01); *A61B 8/4263* (2013.01); *A61B 8/4483* (2013.01); *A61B 8/0833* (2013.01); *A61B 8/4405* (2013.01); *A61B 34/20* (2016.02); *A61N 7/02* (2013.01)

(56) References Cited

U.S. PATENT DOCUMENTS

| | | | |
|---|---|---|---|
| 6,868,195 B2 | 3/2005 | Fujita | |
| 7,245,791 B2 * | 7/2007 | Rambow et al. | 385/12 |
| 8,622,935 B1 * | 1/2014 | Leo | A61B 5/6843 |
| | | | 600/585 |
| 8,864,655 B2 | 10/2014 | Ramamurthy et al. | |
| 8,989,528 B2 | 3/2015 | Udd | |
| 2002/0183592 A1 | 12/2002 | Suzuki et al. | |
| 2004/0165810 A1 | 8/2004 | Fujita | |
| 2009/0123111 A1 | 5/2009 | Udd | |
| 2011/0320570 A1 | 12/2011 | Ewing | |
| 2013/0131499 A1 | 5/2013 | Chan et al. | |

FOREIGN PATENT DOCUMENTS

| | | |
|---|---|---|
| JP | 2003038493 A | 2/2003 |
| JP | 2003116869 A | 4/2003 |
| JP | 2006095172 A | 4/2006 |
| JP | 2008026204 A | 2/2008 |
| JP | 2008173395 A | 7/2008 |
| JP | 2010104426 A | 5/2010 |
| WO | 0133165 A1 | 10/2001 |
| WO | 2006092707 A1 | 8/2008 |
| WO | 2009023801 A1 | 2/2009 |

* cited by examiner

APPARATUS, SYSTEM AND METHOD FOR IMAGING AND TREATMENT USING OPTICAL POSITION SENSING

This disclosure relates to medical devices, and more particularly to medical devices employing fiber optic technology for shape, position, and orientation tracking of imaging and treatment transducer devices.

In ultrasound applications, spatial tracking of transducers has been performed with mechanical sweeping (e.g., an intravenous ultrasound (IVUS) pullback device), image-based registration of data from 2D or 3D probes, infra-red (IR) camera-based stereo-vision, or electromagnetic (EM) sensing. Mechanical devices for constraining transducer motion are cumbersome to use (and can potentially impact image quality since the path defined by the mechanical motion may not coincide with optimal acoustic views). In addition, mechanical devices have limited accuracy that depends on tightly controlled mechanical pullback.

Image-based registration is computationally-intensive and time-consuming, and lowers a possible number of imaging frame rates. Furthermore, image-based registration is limited to tracking relative motions between volumes and cannot provide absolute position estimates of the transducer path (especially when transducer motion occurs over a non-linear surface). IR camera based localization is sensitive to line-of-sight occlusions, limiting its utility, especially for clinical settings in which a clear line of sight between the tracked transducer and the IR cameras cannot be ensured. EM localization exhibits limited spatial accuracy and precision, with a sensitivity to changes in the spatiotemporal characteristics of the local EM environment. These limitations in tracking performance, in turn, impact the capabilities of the ultrasound imaging device in terms of providing high image quality, anatomical accuracy, large fields-of-view, or high temporal frame rates. All of these tracking technologies measure the location of the rigid transducer as a single entity, whereas a tracking technology that allows for sensing of the dynamic shape of the transducer elements would permit flexible transducer configurations with enhanced image acquisition and reconstruction when element tracking data are used in combination with transducer signals in the image formation process.

It would be advantageous to provide systems and methods where positioning and placement of medical devices is reliably performed and where the position sensing can occur in a spatially distributed fashion to allow for flexible imaging arrays that are not possible in conventional probes today.

In accordance with the present principles, an apparatus, system and method for determining a position, orientation or shape includes a transducer device configured to receive signals from a console and generate images based upon reflected waves. A flexible cable is coupled to the transducer device to provide excitation energy to the transducer device from the console. An optical fiber has a shape and position corresponding to a shape and position of the cable during operation. A plurality of sensors is in optical communication with the optical fiber. The sensors are configured to measure deflections and bending in the optical fiber such that the deflections and bending in the optical fiber are employed to determine positional information about the transducer device.

Optical position and orientation sensing of a transducer and tether cabling overcomes the limitations of conventional tracking methods, permitting improved imaging capabilities such as real-time extended field-of-view imaging, live spatial compounding via multi-angle imaging, simultaneous multi-transducer imaging, and enhanced image resolution and quality improvement via shape-enhanced ultrasound beam-forming and reconstruction. Furthermore, optical shape sensing incorporated into the body of a flexible/reconfigurable transducer array will allow for real-time knowledge of transducer geometry that can be used to improve image acquisition and reconstruction while allowing for dynamic adaptation of geometry to suit the clinical application (transducer arrays will not longer be constrained to rigid geometric configurations and allow for non-conventional flexible geometries, e.g., multiple transducer elements distributed over a length of optically-tracked catheter to form a spatially extended deformable transducer array).

An apparatus for determining a position, orientation, and/or shape, includes a transducer device configured to receive signals from a console and generate images based upon reflected or transmitted energy. A flexible cable is coupled to the transducer device to provide excitation energy to the transducer device from the console. At least one optical fiber has a shape and position corresponding to a shape and position of the cable during operation. A plurality of sensors are provided in optical communication with the at least one optical fiber, the sensors being configured to measure deflections and bending in the optical fiber such that the deflections and bending in the optical fiber are employed to determine at least one of a shape and positional information about the transducer device.

Another apparatus for determining a position, orientation, and/or shape, includes a medical instrument, a transducer device configured to receive signals from a console and generate images based upon reflected or transmitted energy and a flexible cable coupled to the transducer device to provide excitation energy to the transducer device from the console. At least one optical fiber has a shape and position corresponding to a shape and position of the medical device during a procedure. At least one other position sensing device is provided for sensing the shape and position of the medical device relative to the at least one optical fiber. A plurality of sensors is in optical communication with the at least one optical fiber, the sensors being configured to measure deflections and bending in the optical fiber such that the deflections and bending in the optical fiber and the at least one other position sensing device are employed to determine at least one of a shape and positional information about the medical device during a procedure.

A system for tracking a portion of an imaging or therapy device includes spatially distributed Fiber Bragg Gratings (FBGs) integrated on an optical fiber and disposed within a flexible cable. An ultrasonic transducer is coupled to an ultrasonic console through the flexible cable. An optical system is configured to deliver light to the FBGs and receive light from the FBGs such that deflections of the optical fiber in the flexible cable are measured. A computer system includes a shape determination program configured to compute parameters related to the deflections of the optical fiber and determine a configuration of the flexible cable such that the configuration of the flexible cable provides a position of the ultrasonic transducer.

A method for tracking of a position of an imaging device includes providing a transducer device configured to receive signals from a console and generate images based upon reflected waves, a flexible cable coupled to the transducer device to provide excitation energy to the transducer device from the console, and at least one optical fiber having a shape and position corresponding to a shape and position of the cable during operation, and a plurality of sensors in optical communication with the at least one optical fiber.

The transducer device is positioned and deflections and bending are measured in the at least one optical fiber which corresponds to the shape and position of the cable such that the deflections and bending in the optical fiber are employed to determine shape and positional information about the transducer device.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

The present disclosure describes systems and methods for position sensing of transducers, transducer elements, or multiple array assemblies. In a particularly useful embodiment, an intravascular ultrasonic transducer is located using fiber optic sensors. The optical sensors may include Fiber Bragg Gratings (FBGs). In one embodiment, an FBG-functionalized ultrasound imaging system employs shape sensing capabilities to allow for new imaging capabilities (e.g., real-time extended field-of-view imaging, spatial compounding via multi-angle imaging, simultaneous multi-transducer imaging, flexible transducer arrays/patches, and enhanced image resolution/quality improvement via shape-enhanced ultrasound beam-forming/reconstruction, etc.).

Optical shape sensing using a multitude of FBG gratings and optical interrogation permits high spatiotemporal resolution tracking of transducer(s) and corresponding cabling/catheter shapes (cabling for transthoracic or body ultrasound, transesophageal echo, or catheter for intracardiac echo to name a few). By comparison, conventional tracking approaches based on electro-magnetism (EM), for example, do not currently exhibit the tracking accuracy or robustness to environmental conditions that is possible with fiber optic shape sensing of position and orientation.

It should be understood that the present invention will be described in terms of medical instruments; however, the teachings of the present invention are much broader and are applicable to any instruments employed in tracking or analyzing complex biological or mechanical systems. In particular, the present principles are applicable to internal ultrasonic procedures of biological systems, procedures in all areas of the body such as the lungs, gastro-intestinal tract, others organs, blood vessels, etc. The teachings are not necessarily limited to ultrasonic sensing, but can also be applied in the development and use of flexible sensor arrays of any other modality, e.g., X-ray detector arrays, scintillator arrays, MR coils, optical sensor arrays (e.g., tracked distribution of optical fiberscopes), etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), and non-volatile storage.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams, state transition diagrams, pseudocode, and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable medium providing program code for use by or in connection with a computer or any instruction execution system. For the purposes of this description, a computer-usable or computer readable medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

In accordance with useful embodiments, tracking sensors for ultrasonic transducers may employ a plurality of different technologies. In accordance with the present principles, optical fiber technologies are described. Optical fiber based sensing of strain can be performed using optical sensors. In one case, the sensors may include FBGs. By integrating strain measurements over a length, a local shape of a length of optical fiber can be determined. Optical measurements of geometry are attractive for at least the following reasons. Measurements are immune to electromagnetic interference and require no electromagnetic emissions. The sensors are passive and therefore intrinsically safe. The ability for multiplexing sensors in an array exists. The possibility of multi-parameter sensing (strain, temperature, pressure, etc.) exists. Distributed sensing is possible, and the sensors have high sensitivity (down to nanostrains when interferometry is used in optical interrogation). In addition, fibers are small and light weight, and are ideal for minimally invasive applications. The fibers are insensitive to variation in signal amplitude (when fiber Bragg sensors are employed with wavelength detection).

For many medical applications, in particular for those requiring minimally-invasive navigation and instrumentation, fiber optic sensing with fiber Bragg gratings offers high-accuracy and high-precision localization at high spatiotemporal resolution along the length of the fiber. Given the light-weight, elongated form factor of optical fiber and its compact cross-sectional footprint, fiber technology provides improvements to ultrasound applications needing transducers tethered to a console via a cable, endoscopic housing, or catheter (ICE). Embedding the fiber Bragg gratings within the body of the cable/endoscope/catheter housing permits fine spatiotemporal tracking of one or more transducer elements/arrays within the elongated medical instrument.

Figure 1:
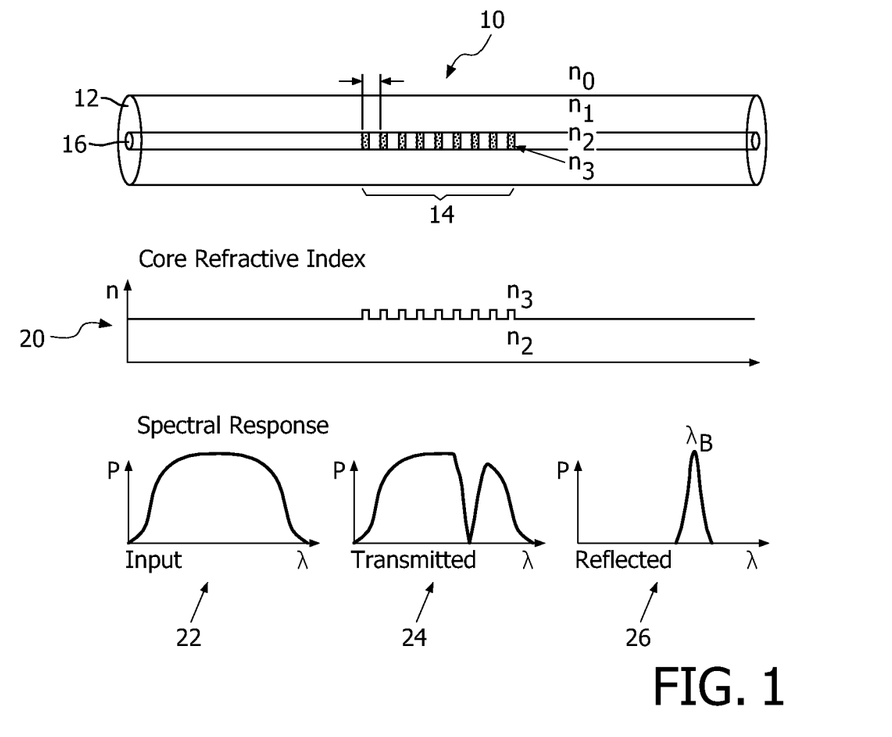
FIG. 1 shows an optical fiber including a Fiber Bragg Grating (FBG), a plot of index of refraction versus distance and spectral response due to the FBG.

Referring now to the drawings in which like numerals represent the same or similar elements and initially to FIG. 1, a Fiber Bragg grating (FBG) 10 is illustratively depicted. In a particularly useful embodiment, the FBG 10 includes a short segment of an optical fiber 12 that reflects particular wavelengths of light and transmits all others. This is achieved by adding a periodic variation 14 of the refractive index in a fiber core 16, which generates a wavelength-specific dielectric mirror. A plot 20 of core refractive index versus distance is illustratively shown.

A fiber Bragg grating 10 can therefore be used as an inline optical filter to block certain wavelengths, or as a wavelength-specific reflector. An input spectrum 22 and respective output spectrums 24 and 26 illustratively show a transmitted portion (spectrum 24) and a reflected portion (spectrum 26) of the input spectrum 22. The fundamental principle behind the operation of a fiber Bragg grating 10 is Fresnel reflection at each of the interfaces where the refractive index changes. For some wavelengths, the reflected light of the various periods is in phase so that constructive interference exists for reflection and consequently, destructive interference exists for transmission.

The Bragg wavelength is sensitive to strain as well as to temperature. This means that Bragg gratings can be used as sensing elements in fiber optical sensors. In a FBG sensor, the strain causes a shift in the Bragg wavelength, $\Delta\lambda_B$. The relative shift in the Bragg wavelength, $\Delta\lambda_B/\lambda_B$, due to an applied strain ($\varepsilon$) and a change in temperature ($\Delta T$) is approximately given by:

$$\frac{\delta\lambda_B}{\lambda_B} = C_s\varepsilon + C_T\Delta T$$

The coefficient $C_s$ is called the coefficient of strain and its magnitude is usually around $0.8\times10^{-6}/\mu\varepsilon$ or in absolute quantities about 1 pm/$\mu\varepsilon$. The coefficient $C_T$ describes the temperature sensitivity of the sensor; it is made up of the thermal expansion coefficient and the thermo-optic effect. Its value is around $7\times10^{-6}/K$ (or as an absolute quantity 13 pm/K). While FBGs are particularly suited for use in accordance with the present principles, other sensors may also be employed.

Figure 2:
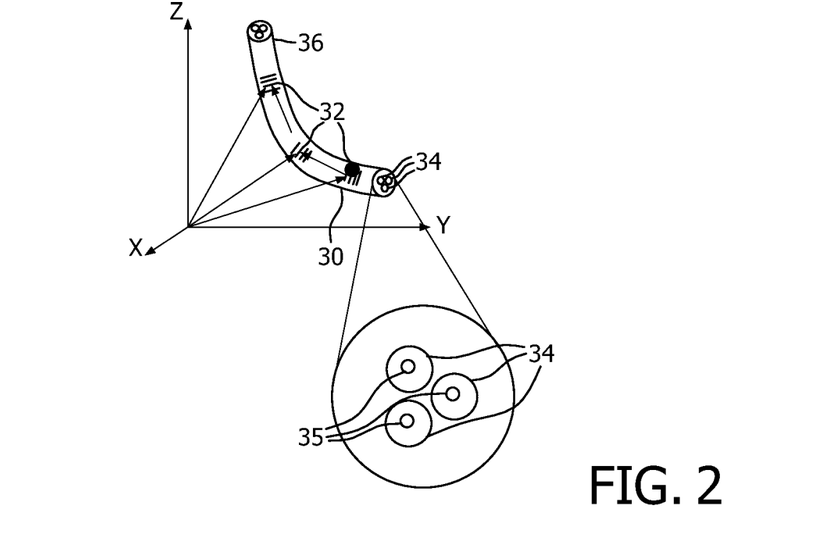
FIG. 2 shows a fiber triplet deflected in three-dimensional space.

Referring to FIG. 2, a fiber triplet 30 includes three fibers 34 and three FBGs 32. One advantage of employing the triplet 30 or a multiple fiber/FBG element is that various sensor elements can be distributed over the length of a fiber. For example, incorporating three cores with various sensors (gauges) along the length of the fiber embedded in a structure, the three dimensional form of such a structure can be precisely determined. Along a length of a fiber 34 at various positions, FBG sensors 32 are located. From the strain measurement of each FBG 32, the curvature of the structure 30 can be inferred at that position in three dimensional space (x, y, z). From the multitude of measured positions, the total three dimensional form is determined.

The fibers 34 are preferably potted in a flexible material, such as medical grade polymers (e.g., PEEK™). Fiber cores 35 are shown in an inset cross-sectional view. A sheath 36 surrounding the fibers may be constructed from medical grade polymers, silicone, or other suitable materials.

Figure 3:
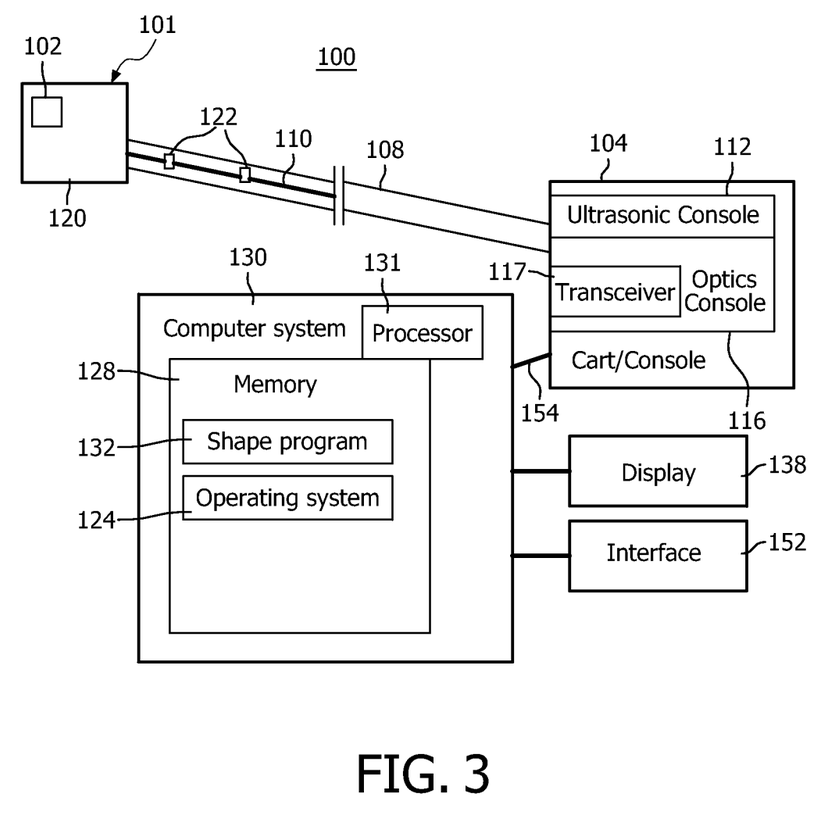
FIG. 3 is a diagram showing a system for determining a position of an ultrasonic probe in accordance with one illustrative embodiment.

Referring to FIG. 3, an imaging or treatment system 100 is illustratively depicted with ultrasound transducers in accordance with one illustrative embodiment. System 100 includes a medical imaging device 101 with guidance feedback through shape sensing. The device 101 includes one or more transducer elements 102. Device 1010 may be employed for treatment procedures in other embodiments. The transducer elements 102 may include piezoelectric transducer elements that generate ultrasonic energy in response to electric impulses. It should be understood that other forms of mechanical and electromagnetic energy may be employed and that the transducer elements may include other structures. The transducer elements 102 may be connected to a cart/console 104 via a cable 108. The cable 108 may include an endoscope housing or other medical device, a catheter or other flexible member. Cable 108 includes at least one optical shape sensing fiber 110 embedded therein for real-time high accuracy spatial localization of the transducer elements 102 and associated cabling (108).

The transducer elements 102 are housed in a flexible assembly 120. The cart/console 104 includes an ultrasound console 112 which is configured to supply the energy to drive the transducer elements 102 which generate ultrasonic waves. The shape sensing fiber or fiber bundles 110 extend along at least a portion of the cable 108 and interconnect to the console 104 to allow for accurate, real-time assessment of transducer element geometries and dynamics.

The console 104 includes an optical console 116 that delivers light to optical sensors 122 (e.g., FBGs) of the fiber bundles and receives light from them. An optical source at the console 116 (or other location, if desired) is provided for shape sensing fiber illumination. An optical interrogation unit receiver (such as a transceiver 117) is provided in console 116 to read out multiplexed signals returning from FBGs 122 in all fibers 110.

Console 116 may be connected to computer system 130 which includes memory storage 128 and an operating system 124 with a corresponding shape determination program 132 which calculates parameters related to the deflection of the optical fibers 110. Computer system 130 may include console 116 or be an independent system. The optical transreceiver 117 transmits and receives optical signals to/from the fibers 110. The light signals are interpreted to determine a shape of the fiber and thereby determine a position or orientation of the transducer element 102 in a body. Data from sensors 122 is transmitted through the optical fibers 110 and may be correlated with a 3D volume or map or a reference position (e.g., the cart 104) to determine position information on the transducer elements 102 or of the cable 108.

The computer 130 includes a processor 131 that implements real-time FBG sensing methods 132 for sensing fiber deflection and deriving the corresponding shapes of the fiber bundles, and computes spatial geometry of the one or more transducer elements 102 forming an extended transducer array. The computer 130 computes spatially-localized 3D ultrasound datasets based on the computed spatial geometry of the one or more transducer elements 102. An input/output (I/O) device or interface 152 provides for real-time interaction with the computer 130, the device 101 and a visual display 138 of spatially-localized ultrasound imaging, and an orientation, shape and/or position of the cable 108 may be displayed. Computer system 130 may include the user interface 152 for interacting with the console 116, console 112, and the device 101. The interface 152 may include a keyboard, a mouse, a touch screen system, etc.

A data connection 154 connects the ultrasound console 112, optical interrogation unit 117 and console 116 with processor 131 for determination of transducer geometry/shape. The optical interrogation unit or console 116 provides real-time spatial localization data to the ultrasound console 112 for dynamic reconstruction of spatially accurate ultrasound data in 3D for enhancements. The enhancements may include a real-time extended field-of-view imaging; live spatial compounding via multi-angle imaging; simultaneous multi-transducer imaging; augmented image resolution/quality improvement via shape-enhanced ultrasound beamforming/reconstruction (e.g. ultrasonic tomographic reconstruction). The flexible assembly of transducer elements 102 may be conformed to the relevant patient anatomy (e.g. skin surface, tortuous vascular anatomy, GI tract, etc). The optical shape fiber 110 allows for accurate determination of one or more transducers 102 relative to one another and relative to a fixed reference location (e.g., an ultrasound cart reference) to enhance imaging performance.

Figure 4:
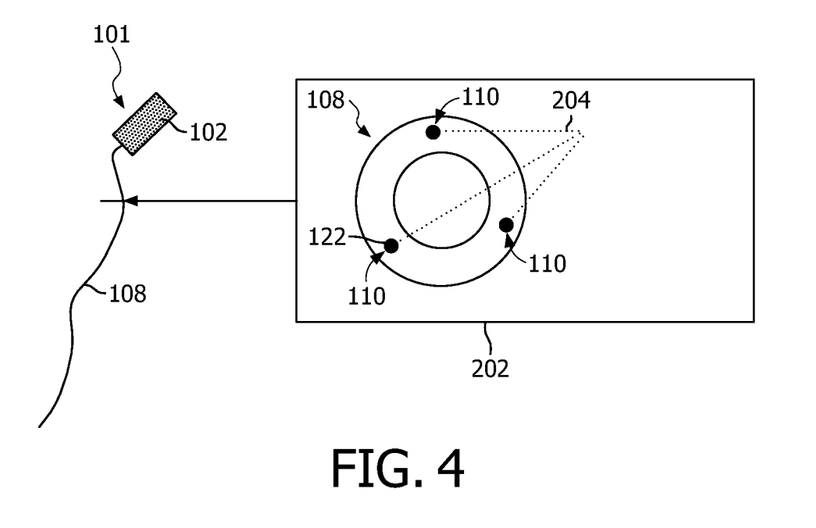
FIG. 4 is a diagram showing an ultrasonic device and a cross-sectional view of a cable having an optical sensor assembly in accordance with one embodiment.

Referring to FIG. 4, device 101 is shown in accordance one illustrative embodiment. In this embodiment, device 101 includes a single transducer element 102. Transducer element 102 is coupled to a cable 108, which may include a catheter, an endoscope, etc. Cable 108 includes at least one strain/shape sensing assembly therein. Detail 202 shows a cross-sectional view of the cable 108. Strain/shape sensing assembly 204 includes fibers 110 with sensors (e.g., FBGs) 122 which permit optical sensing of strain and shape. In the illustrative embodiment of FIG. 4, sensing assembly 204 includes a fiber triplet to better track the shape, rotation and position of the fiber Bragg gratings. Device 101 includes sensing assembly 204 along with ultrasound transducer elements 102. In this way, based on the positional information provided by the sensing assembly 204, the positions and orientations of the transducer elements 102 can be determined relative to a reference and tracked throughout a procedure. Recorded images may now include shape/positional information along with the ultrasonic images in real-time or for later retrieval.

The transducer elements 102 may be included in an elongated ultrasound probe, e.g., in a hand-held, endoscopic, or catheter assembly connected to the ultrasound cart (104, FIG. 3) which includes the optical source and interrogation unit (117, FIG. 3). Sensing assembly 204 is embedded along the length of the housing/cabling 108 to allow for localization of the device 101, followed by visualization of the spatially-tracked and reconstructed ultrasound data in 3D.

Figure 5:
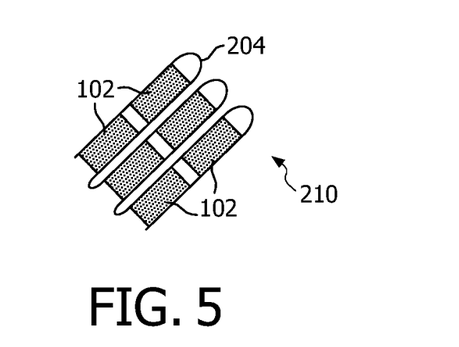
FIG. 5 is a diagram showing an ultrasonic device having a plurality of transducer elements coupled to a single optical sensor assembly in accordance with another embodiment.

Referring to FIG. 5, an ultrasound probe 210 includes a plurality of transducer elements 102 arranged in an extended geometry. The geometry may include a one-dimensional distribution of elements 102 along a length of a catheter (e.g., an Intracardiac Echocardiography (ICE) catheter), a probe (e.g., a transesophageal echocardiography (TEE) probe), etc. or may include a multiple dimensioned flexible patch probe that conforms to patient anatomy, (e.g., a flexible carotid probe that wraps around the patients neck) or another other configuration. Another geometry may include the combination of existing imaging probes, such as TEE with ICE or ICE with transthoracic echocardiogram (TTE), etc. and all other permutations. Optical shape fiber assembly 204 interconnects the transducers 102 in this assembly to permit high-accuracy tracking of relative transducer motion. With this information, body surfaces and other information may be collected along with ultrasonic imaging data. This configuration permits for optimization of multi-transducer acquisition and reconstruction by exploiting simultaneous firing/receiving of array elements in combination with 3D location information.

Figure 6:
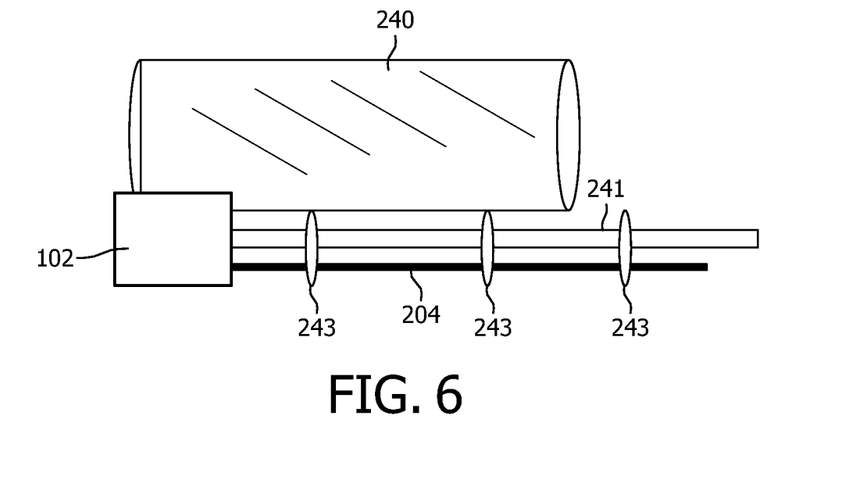
FIG. 6 is a diagram showing an ultrasonic device connected with a form fitting sheath so that a cable for the ultrasonic device and an optical fiber sensor assembly coincide in accordance with another embodiment.

Referring to FIG. 6, the embodiments described herein may be employed or connected to a form fitting sheath 240 that elastically or through other means of secure attachment is connected to an ultrasound transducer element(s) 102. The transducer element 102 is fixed with respect to the sheath 240. The sheath 240 may include a cuff, glove, etc. to attach to a users or patients body. The sheath 240 is tied to an ultrasonic cable 241 and connects with an ultrasonic console to be powered. A sensing assembly 204 is coupled to the cable 241 using connectors 243, or alternately the sheath 240 can be extended and cable 241 and assembly 204 may be placed inside the sheath 240 so that they are coincident and remain such during operations or procedures. In this way, the movement of the transducer element 102 is determined with the position of cable 241 using the sensor assembly 204. A light source (not shown) at a reference position is employed to illuminate the optical sensor assembly 204 to determine strains in the optical fiber to provide the shape and position of the cable 241 and therefore the transducer element 102. One advantage of this embodiment is that it permits retrofitting of existing transducers or probes.

Figure 7:
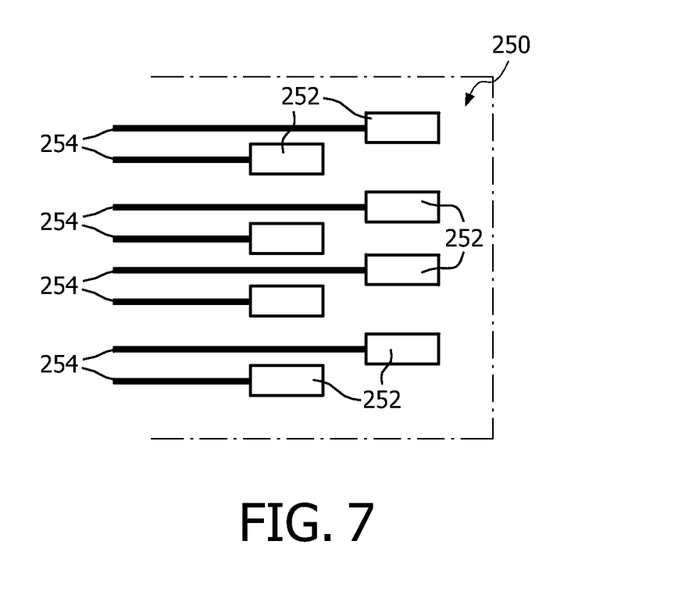
FIG. 7 is a diagram showing an ultrasonic device having a plurality of transducer elements each coupled to their own optical sensor assembly in accordance with another embodiment.

Referring to FIG. 7, a High Intensity Focused Ultrasound (HIFU) transducer 250 may be employed whose independent elements 252 are tracked separately by multiple fibers 254 (e.g., sensor assemblies 204). The fibers 254 include FBGs to determine shape and position and described above. This embodiment permits identification of position (and shape) for each of the plurality of elements 252, and allows for flexible geometries where the transducer elements 252 can be positioned so that they are not obscured by bone (as in the ribs) or air filled paths (such as lungs or bowels). The ability to monitor their position with accuracies on the order of less than 500 microns allows for uncertainties in phase of about ⅓ of a cycle. With accuracies of less than 250 microns, phasing can be obtained that is adequate for additive HIFU phases resulting in the ability to heat tissue and therefore provide treatment for a patient. Other treatments may also be provided, e.g., ultrasonic treatments, etc.

Figure 8:
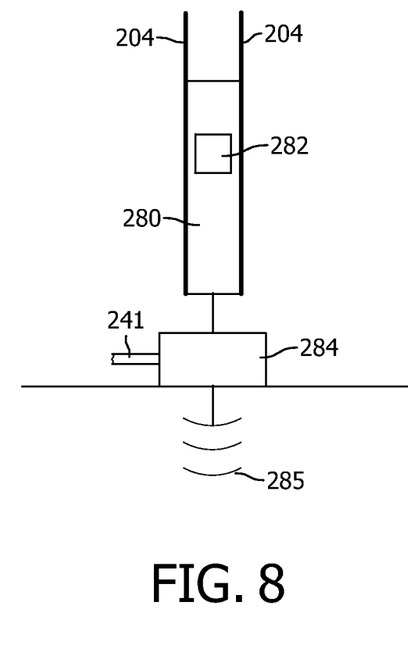
FIG. 8 is a diagram showing an ultrasonic device, a medical device and at least one optical sensor assembly employed for guidance of the medical device in accordance with another embodiment.

Referring to FIG. 8, a device 280, which may include a needle, catheter, etc. includes a shape sensing assembly 204 with fibers 110 and sensors 122 (FIGS. 3, 4). The device 280 is imaged with ultrasound. In this embodiment, the relative positions of the device 280 and the fiber (204) are measured with two optical fibers (assemblies 204), or combinations of optical fibers and EM sensors 282. The device's position is determined and the relative angle between the device 282 and an ultrasound transducer 284 is calculated. If the device 280 is off-perpendicular, it is expected that the majority of the ultrasound signal 285 will reflect away from the transducer 284. However, a component of the signal will reflect towards the transducer 284. By sensing the relative orientation of the entire length of the device and the transducer, one can employ beam forming techniques where only channels that are expected to be perpendicular are included in the beam summing process. In addition, by knowing the relative position of the device 280, beam forming can be only applied to a portion of the image allowing for optimized "hard reflector" imaging and "soft scatterer" imaging within a same image formation.

Figure 9:
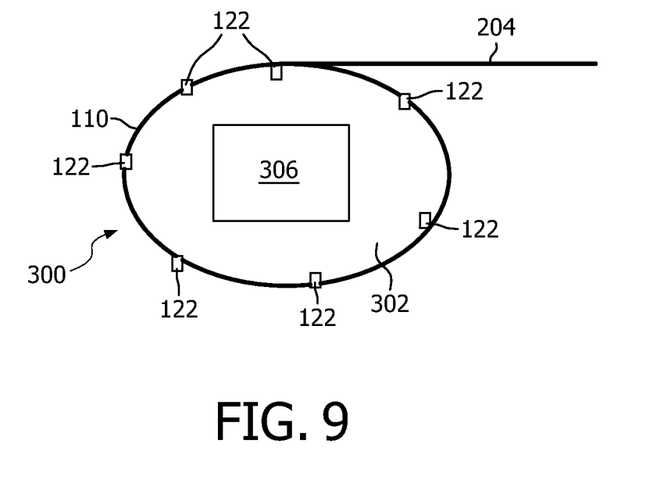
FIG. 9 is a diagram showing optical sensors formed into an array to detect an applied pressure of a transducer element in accordance with another embodiment.

Referring to FIG. 9, a patch 300 includes an optical fiber oriented in a circular or other closed or partially closed formation. The patch 300 is placed on a patient with an acoustic window 302 in the center. The deformation of skin from applied pressure of a transducer 306 along with the knowledge of the relative position of the patch 300 and the transducer 306 (with respect to a console 104 or 112, FIG. 3) would allow not only for spatial registration but for recreatable pressure (actually strain) to be applied to the patient. Pressure (or the pushing of the ultrasound transducer (s) 306) is often needed to obtain an optimal acoustic path and to provide good acoustic coupling to the patient. This embodiment could help coach less experienced operators, provide for the ability to regain an acoustic view for patients in monitoring situations; and be used in closed feedback loops such as robotics where the controller will need to know how much pressure to apply to the patient with the transducer. It should be understood that other configurations and embodiments are contemplated within the scope of the present claims. The present embodiments are applicable to all ultrasound imaging techniques for interventional applications using tethering to an ultrasound cart.

Figure 10:
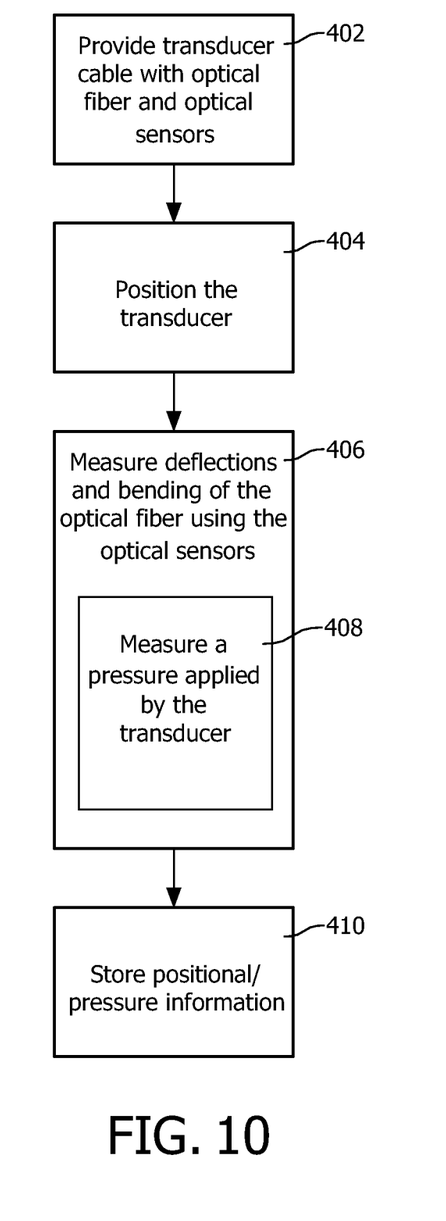
FIG. 10 is a block/flow diagram showing a method for determining a position of an ultrasonic device in accordance with the present principles.

Referring to FIG. 10, a method for tracking of a position of an imaging device, such as an ultrasonic transducer is shown. In block 402, a device is provided. The device includes a transducer device configured to receive signals from a console and generate images based upon reflected waves. A flexible cable is coupled to the transducer device to provide excitation energy to the transducer device from the console, and at least one optical fiber has a shape, orientation and position corresponding to a shape, orientation and position of the cable during operation. A plurality of sensors are also provided in optical communication with the at least one optical fiber. In block 404, the transducer device is positioned. In block 406, deflections and bending in the at least one optical fiber correspond to the shape, orientation and position of the cable. The deflections and bending experienced by the cable are experienced by the optical fiber as well. The deflections and bending in the optical fiber are employed to determine positional information about the transducer device. The sensors preferably include a plurality of Fiber Bragg Gratings distributed over a length of the optical fiber and the deflections and bending are measured using the Fiber Bragg Gratings.

In alternate embodiments, different fiber and transducer configurations may be employed to measure different parameters. In one embodiment, the at least one optical fiber includes a plurality of sensors formed in a closed or partially closed formation and the method includes placing the transducer device among the plurality of sensors to measure position changes due to a pressure applied to the transducer device in block 408. In block 410, the positional (and/or the pressure) information may be stored. The positional and pressure information may be stored along with ultrasonic images or images from other technologies.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for an apparatus, system and method for imaging and treatment using optical position sensing (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An apparatus for determining a position, orientation, and/or shape, comprising:
   a medical device;
   a transducer device, said transducer device being configured to receive signals from a console and generate images based upon reflected or transmitted energy;
   a flexible cable coupled to the transducer device to provide excitation energy to the transducer device from the console;
   at least one optical fiber having a shape and position corresponding to a shape and position of the medical device during a procedure;
   at least one other position sensing device, said at least one other position sensing device being configured for sensing the shape and position of the medical device relative to the at least one optical fiber; and
   a plurality of sensors in optical communication with the at least one optical fiber, the sensors being configured to measure deflections and bending in the optical fiber such that the deflections and bending in the optical fiber and the at least one other position sensing device are employed to determine at least one of a shape and positional information about the medical device during a procedure.

2. The apparatus as recited in claim 1, wherein the plurality of sensors includes Fiber Bragg Gratings distributed over a length of the at least one fiber to measure strain.

3. The apparatus as recited in claim 1, wherein the at least one fiber includes a fiber triplet.

4. The apparatus as recited in claim 1, wherein the at least one other position sensing device includes one of another optical fiber with optical sensors and an electromagnetic sensor.

* * * * *